United States Patent [19]

Givens et al.

[11] Patent Number: 5,105,154

[45] Date of Patent: * Apr. 14, 1992

[54] APPARATUS FOR MEASURING RADIAL RESISTIVITIES IN CYLINDRICAL CORE SAMPLES OF POROUS ROCK

[75] Inventors: Wyatt W. Givens, Dallas; W. David Kennedy, Carrollton, both of Tex.

[73] Assignee: Mobil Oil Corporation, Fairfax, Va.

[*] Notice: The portion of the term of this patent subsequent to Mar. 3, 2009 has been disclaimed.

[21] Appl. No.: 671,340

[22] Filed: Mar. 19, 1991

[51] Int. Cl.$^5$ .............................................. G01V 3/02
[52] U.S. Cl. ........................................ 324/376; 73/153
[58] Field of Search ................... 324/376; 73/151, 153

[56] References Cited

U.S. PATENT DOCUMENTS

| | | | |
|---|---|---|---|
| 2,802,172 | 8/1957 | Mueller et al. | 324/376 |
| 4,628,267 | 12/1986 | Lee et al. | 324/376 |
| 4,686,477 | 8/1987 | Givens et al. | 324/376 X |
| 4,907,448 | 3/1990 | Givens | 324/376 |
| 4,924,187 | 5/1990 | Sprunt et al. | 324/376 |
| 4,926,128 | 5/1990 | Givens | 324/376 |

FOREIGN PATENT DOCUMENTS 510561  3/1955  Canada .............................. 324/376

OTHER PUBLICATIONS

Marinelli et al., "Core Tester Contact Assembly", *IBM/TDB*, vol. 9, No. 3, Aug. 1966, pp. 296-297.

*Primary Examiner*—Kenneth A. Wieder
*Assistant Examiner*—Warren S. Edmonds
*Attorney, Agent, or Firm*—Alexander J. McKillop; Charles J. Speciale; George W. Hager, Jr.

[57] ABSTRACT

A cylindrical core sample of a subterranean formation is place into a sleeve under confining pressure. At least one electrode array extends through the sleeve and makes contact with the core sample. The array is in a plane normal to the core sample and has an even number of electrodes equally spaced about the sleeve. A current is passed through the core sample and voltages are measured across each pair of electrodes that are spaced 180° apart around the sleeve. Such measurements are utilized to identify the radial direction of any electrical anisotropy in the core sample, particularly under differing fluid saturation conditions.

15 Claims, 2 Drawing Sheets

APPARATUS FOR MEASURING RADIAL RESISTIVITIES IN CYLINDRICAL CORE SAMPLES OF POROUS ROCK

BACKGROUND OF THE INVENTION

This invention relates to the area of oil and natural gas exploration and, more particularly, to apparatus for identifying regions of rock formations from which hydrocarbons may be produced.

Hydrocarbon saturation $S_o$ is generally determined from a measured water saturation $S_w$ as follows:

$$S_o = 1 - S_w. \tag{1}$$

Water saturation present in a subterranean formation is typically determined from interpretation of conventional electrical (i.e., resistivity) logs recorded in a borehole drilled through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54–62, 1942, by G. E. Archie. This equation is expressed as follows:

$$S_w{}^n = R_w / \phi^m R_t, \tag{2}$$

where $S_w$ is the fractional water saturation (i.e. free and bound water of the formation expressed as a percent of the available pore space of the formation), $R_w$ is the formation water resistivity, $\phi$ is the formation porosity, $R_t$ is the formation electrical resistivity, n is the saturation exponent and m is the porosity or cementation exponent. The Archie equation may be expressed in other ways and there are numerous methods in the art for determining, measuring or otherwise obtaining the various components needed to predict fractional water saturation $S_w$ from the formation resistivity, $R_t$, using the equation in any of its forms.

Archie defined two quantities that provided the basis for his water saturation equation (1). The first quantity is the formation factor F which defines the effect of the rock matrix on the resistivity of water as follows:

$$F = R_o R_w, \tag{3}$$

where
$R_o$ = resistivity of water saturated rock and
$R_w$ = water resistivity.

Archie reasoned that for a given value of $R_w$, the formation factor F would decrease with increasing porosity, $\phi$, to some exponent m:

$$F = 1/\phi^m. \tag{4}$$

This porosity exponent m has also become known as the Archie cementation exponent. Thus Archie provided a useful characterization of a rock fully saturated with a conducting brine in terms of the water resistivity $R_w$, porosity $\phi$, and a rock parameter m. It is important to note that Archie assumed all conductance to be in the brine.

The second quantity is the resistivity index I defined as the ratio of the resistivity of a rock partially saturated with water and hydrocarbon, $R_t$, to the same rock saturated fully with water, $R_o$, as follows:

$$I = R_t / R_o. \tag{5}$$

Archie reasoned that as the water saturation decreased (i.e. hydrocarbon saturation increased) the resistivity $R_t$ and hence I would increase to some exponent n:

$$I = 1/S_w{}^n \tag{6}$$

where $S_w$ = volume of water in pores/total pore volume. This exponent n has become known as the Archie saturation exponent. It is again important to note that Archie assumed all conductance to be in the brine and further that all pores within the rock have the same water saturation $S_w$.

It is these two equations (4) and (6) for the formation factor F and resistivity index I respectively that Archie combined to provide the water saturation expression $S_w$ of equation (2). Certain logs have provided formation resistivity $R_t$ and porosity $\phi$. Water samples provide the best values for $R_w$. Standard practice is to measure rock sample resistivities $R_o$ and $R_t$ for a number of water saturations and to plot the logarithm of I versus the logarithm of $S_w$. Archie s equations assume such a logarithmic plot can be fit by a straight line with slope of $-n$.

Many core samples are, however, not homogenous and electrically isotropic. For such core samples, the Archie saturation exponent n will be strongly dependent on the direction the resistivity measurement is made. For example, a saturation exponent measured across permeability barriers within a core sample may be one and a half times as large as if it were measured parallel to the permeability barriers. This difference can have a large detrimental effect on the determination of hydrocarbon reserves derived from the calculated water saturation of equation (2). It is, therefore, an object of the present invention to determine resistivity of a core sample that is not electrically anisotropic and to identify the degree of anisotropy changes as the brine saturation of the core sample changes so that an accurate water saturation can be calculated from equation (2).

SUMMARY OF THE INVENTION

The present invention is directed to apparatus for measuring electrical anisotropy of a core sample of a subterranean formation and, more particularly, to measuring the resistivity of a fluid saturated porous rock under confining pressure as an indication of core sample electrical anisotropy.

In an initial aspect, a sleeve contains a cylindrically-shaped core sample through which an electric current is passed. At least one electrode array extends through the sleeve and makes contact with the outer surface of the core sample. The array is in a plane normal to the cylindrical axis of the core sample and has an even number of electrodes equally spaced along the sleeve. Voltages are measured across each pair of electrodes in the array that are spaced 180 apart around the sleeve. Each electrode is molded into the sleeve with a spherical-like portion protruding out of the inner surface of the sleeve and making contact with the outer surface of the core sample.

In a more specific aspect, each electrode comprises a cylindrical main body member and a semispherical end member with diameter greater than that of the main body member such that the flat portion of said semispherical end member is adjacent to the main body member and normal to the cylindrical axis of the main body member.

In a further aspect, a fluid inlet is positioned in a first end of the sleeve through which a displacing fluid is injected under pressure into the core samples to displace the initial saturating fluid in the core sample, such displacing fluid being immiscible with and of differing electrical conductance to the initial saturating fluid. A porous member is positioned in a second end of the sleeve through which the initial saturating fluid is discharged from the core sample, such porous member being impermeable to the discharging fluid. A plurality of electrode arrays extend through the sleeve at spaced-apart positions along the length of the sleeve and make contact with the outer surface of the core sample at such spaced-apart positions. Each of the arrays is in a plane normal to the cylindrical axis of the core sample. A confining pressure is applied through the sleeve to the core sample as the electric current is passed therethrough. Resistivities determined from the voltages measured across each pair of electrodes in each array are used to identify the radial component of any electrical anisotropy within the core sample in the plane of each of the electrode arrays and along the length of the core sample between such arrays.

DESCRIPTION OF THE PREFERRED EMBODIMENT

Figure 1:
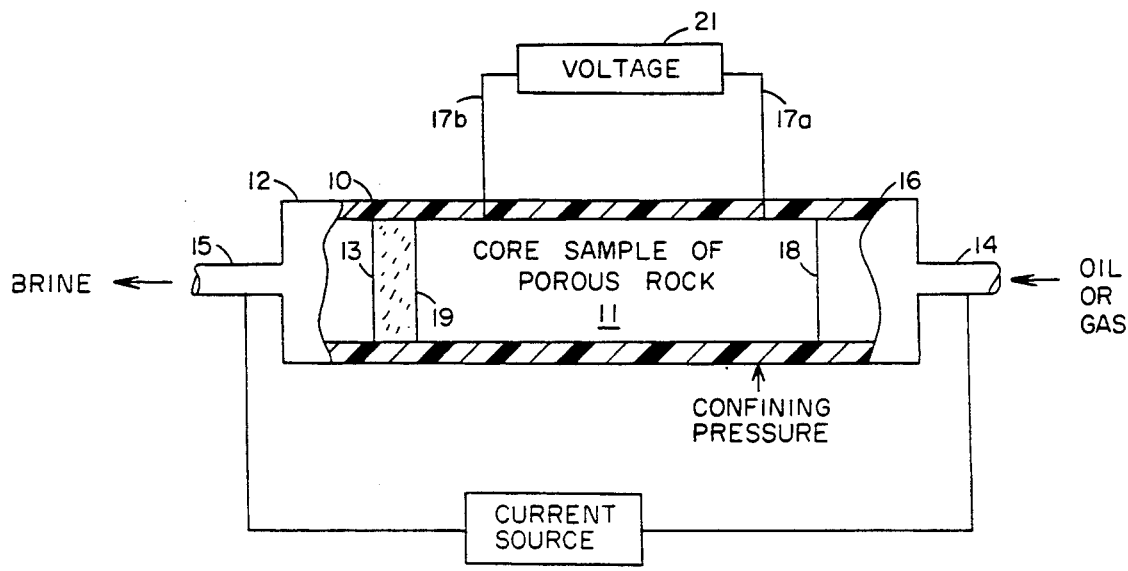
FIG. 1 illustrates prior art apparatus for carrying out resistivity measurements on core samples of subterranean formations.

A system that has been successfully used in carrying out linear resistivity measurements along a core sample from a subterranean formation is shown in FIG. 1 (prior art). A pressure sleeve 10, preferably natural or synthetic rubber, surrounds a cylindrical core sample 11 of a porous rock to be measured for resistivity at a plurality of fluid saturations. Positioned between the core sample 11 and end 12 of the pressure sleeve 10 is a porous member 13, which is permeable to a first fluid saturating the core sample, but is impermeable to a second fluid used to displace the first fluid from the core sample. The second, or displacing fluid, is immiscible with the first fluid saturating the core sample and is of different electrical conductivity. This first saturation fluid is the wetting fluid for the porous member 13, which by way of example, may be a ceramic plate or a membrane. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al., the teachings of which are incorporated herein by reference. Through such a pressure vessel a pressure is applied to the sleeve 10 and hence to the porous rock 11. The pressure should be sufficient to eliminate any fluid annulus between the sleeve 10 and the surface of the core sample. A fluid inlet 14 and a fluid outlet 15 feed into the ends 16 and 12 respectively of the sleeve 10. Both inlet 14 and outlet 15 also serve as current conducting electrodes for passing current from a source 20 through the porous rock 11. A pair of voltage electrodes 17a and 17b penetrate sleeve 10 and make contact with the porous rock at spaced locations along the length of the porous rock. The voltage across the porous rock 11 between the electrodes 17a and 17b is measured by the unit 21.

The core sample of porous rock 11 is initially fully saturated, by way of example, with an electrically conducting fluid, such as salt water, and placed under confining pressure. A current is passed through the porous rock and a voltage along the length of the porous rock is measured between electrodes 17a and 17b. Such voltage measurement may be carried out in accordance with the teachings of U.S. Pat. No. 4,467,642 to Givens; U.S. Pat. No. 4,546,318 to Bowden and U.S. Pat. No. 4,686,477 to Givens et al, the teachings of which are incorporated herein by reference. The resistivity, or its reciprocal conductivity, of the porous rock is determined using the measured voltage, the length, and the cross-sectional area of the core. A displacing fluid such as a nonconducting oil or gas, may then be forced through inlet 14 into end 18 of porous rock 11 to change the fluid saturation condition prior to the making of the next resistivity measurement.

Typical of such a resistivity measuring system of FIG. 1 are those described in U.S. Pat. Nos. 4,907,448 and 4,926,128 to Givens and U.S. Pat. No. 4,924,187 to Sprunt et al.

Having now described a typical resistivity measurement carried out in a single direction along the axial direction of a cylindrical core sample as shown in FIG. 1, the present invention of providing tensor components of resistivity, or conductivity, needed for interpreting electric logs of a subterranean formation with anisotropic properties by measuring and comparing resistivity measurements in a plurality of radial directions through a cylindrical core sample of the formation and normal to its cylindrical axis will now be described. A transversely isotopic cylindrical core sample of the formation is cut so that the formation bedding plane is at an angle to the cylindrical axis of the core sample. The core sample is initially saturated with an electrically conducting fluid such as salt water, and placed within sleeve 10 under confining pressure representative of in-situ pressure. The core sample is contacted with an array of electrodes contained by sleeve 10 at each of a plurality of spaced-apart positions along the length of the core sample, such as electrode arrays A, B and C of FIG. 2 for example. Each such array A–C lies in a plane normal to the axis of the core sample and the electrodes in each array are equally spaced at an even number of positions about the sleeve 10.

Figure 2:
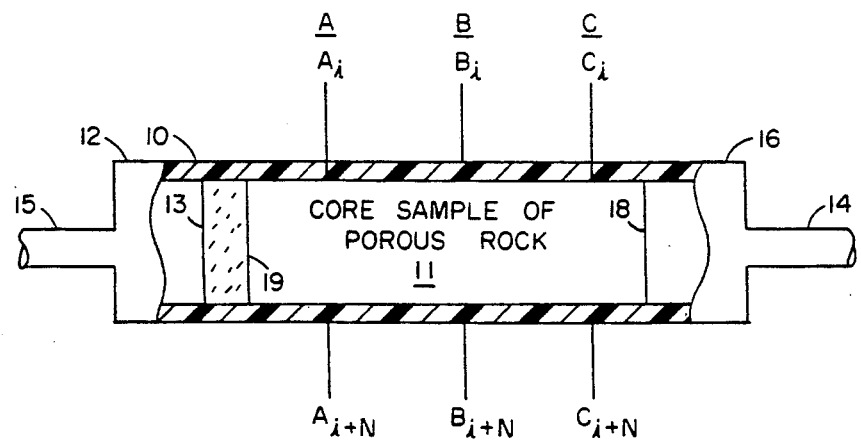
FIG. 2 illustrates apparatus employing electrode arrays for carrying out resistivity measurements on electrically anisotropic core samples of subterranean formations in accordance with the present invention.
Figure 3:
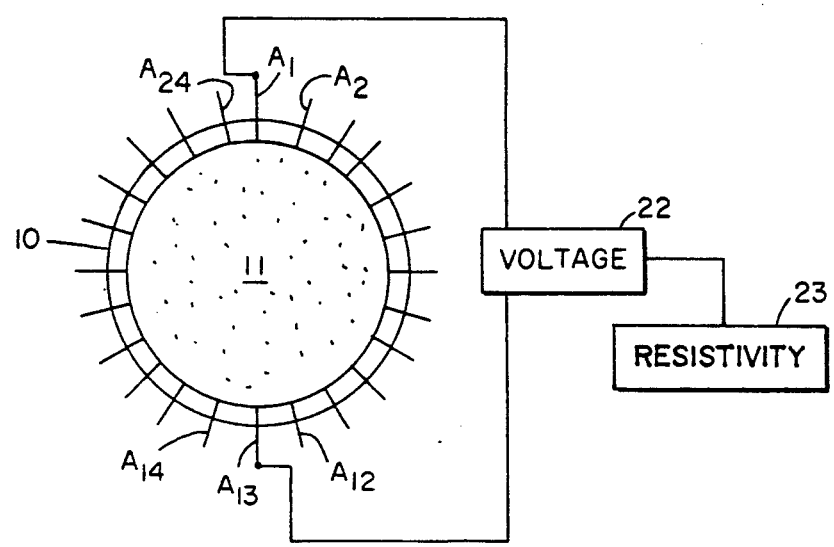
FIG. 3 is a cross-sectional view through the apparatus of FIG. 2 showing in detail one of the electrode arrays of FIG. 2.

FIG. 2 shows a pair of such electrodes $A_i$ and $A_{1+N}$ which are spaced-apart 180° about sleeve 10 (with i=1 to N). FIG. 3 is a cross-sectional view taken through the sleeve 10 and core sample 11 at the axial position of array A with 24 electrodes $A_1$–$A_{24}$ being shown (cross-sectioning of sleeve 10 being omitted for clarity). As can be seen in FIG. 3 there are 12 electrode pairs at 180° spaced-apart positions about sleeve 10 such as electrode pairs $A_1$ and $A_{13}$, $A_2$ and $A_{14}$–$A_{12}$ and $A_{24}$. A current is passed through core sample 11 and a voltage is measured across each of the $A_i$ and $A_{1+N}$, $B_i$ and $B_{i+N}$, and $C_i$ and $C_{i+N}$ electrode pairs spaced-apart 180° about the arrays A, B and C such as shown by voltage unit 22 across electrode pair $A_1-A_{13}$ for example. These voltages as well as a voltage measured along the axial length of the core sample by unit 21, such as shown in FIG. 1, are sued by a resistivity unit 23 to determine the electrical resistivities of the core sample both along the core sample and in the plurality of radial directions through the core sample normal to core sample axis between the electrodes of each corresponding electrode pair. Following these measurements, the fluid saturation in the core sample may be altered any number of times with such measurements being repeated for each differing fluid saturation.

From the voltages measured normal to the axis of the core sample at a plurality of positions along the axis of the core sample the desired tensor components of resistivity, or conductivity, needed for interpreting electric logs of subterranean formations with anisotropic properties are determined. Core samples cut parallel and perpendicular to visible bedding planes at neighboring locations might be used to indicate and measure electrical anisotropy. However, such a procedure cannot be definitive because the samples might differ in their electrical properties regardless of how close together they resided in the original rock, and it would be difficult to obtain the same partial water saturations in each core sample for comparison measurements. A single cylindrical core sample cut with the bedding plane at an angle to the axis of the core sample as described above is utilized in accordance with the present invention to overcome such limitations.

Figure 4:
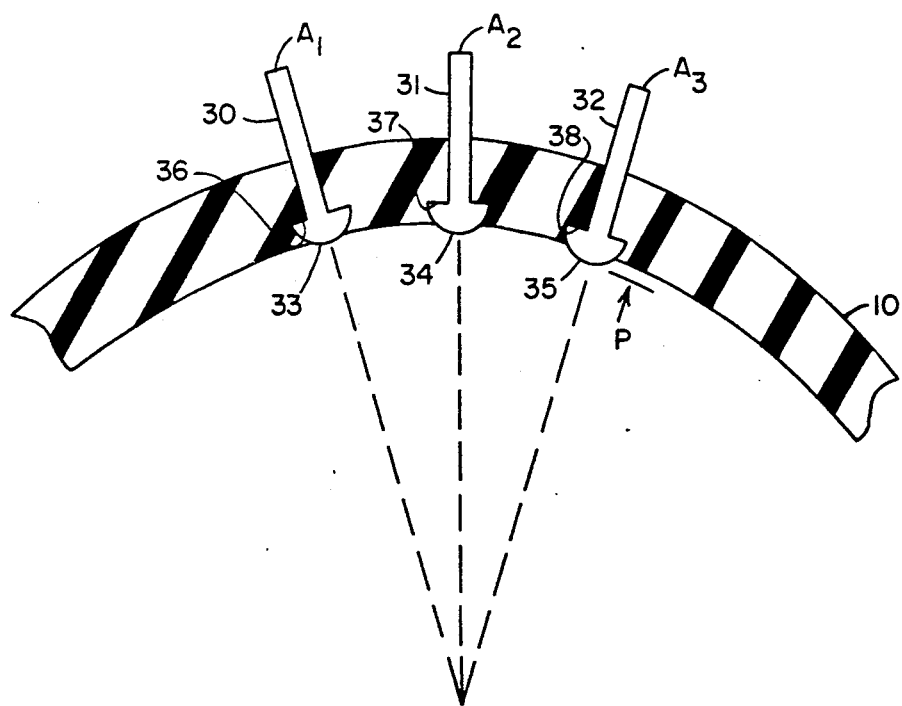
FIG. 4 illustrates one configuration for the electrodes of each of the electrode arrays of FIGS. 2 and 3.

Referring now to FIG. 4, there is shown a preferred configuration for the electrodes of each of the electrode arrays A-C. For purpose of example, electrodes $A_1-A_3$ are shown molded into a rubber sleeve 10 with cylindrical main body members 30-32 and spherical-like end members 33-35 for making contact with the outer surface of a core sample by extending outward from the inner surface of sleeve 10 by a distance d. As shown in FIG. 4, end members 33-35 are semispherical with recessed portions, or lips, 36-38, being normal to the outer surface of the cylindrical main body members 30-32. Such a semispherical end member provides for enhanced adhesion to the rubber sleeve 10.

While the foregoing has described a preferred embodiment of the present invention, it is to be understood that various modifications or changes may be made without departing from the spirit and scope of the invention as set forth in the appended claims.

We claim:

1. Apparatus for determining resistivity of a core sample of a subterranean formation, comprising:
   a) a sleeve containing a cylindrical core sample of a subterranean formation,
   b) means for applying a current through said core sample,
   c) means for measuring voltages in a plurality of radial directions through said core sample normal to the cylindrical axis of said core sample in response to the flow of said current through said core sample, and
   d) means for determining electrical resistivities in said plurality of radial directions through said core sample from said measured voltages.

2. The apparatus of claim 1 wherein said voltage measuring means comprises:
   a) at least one electrode array extending through said sleeve and making contact with the outer surface of said core sample, said array being in a plane normal to the cylindrical axis of said core sample and having an even number of electrodes equally spaced around said sleeve, and
   b) means connected to said electrodes for measuring the voltage across each pair of electrodes that are spaced 180° apart around said sleeve in response to the flow of said current through said core sample.

3. The apparatus of claim 2 wherein each of said electrodes is molded into said sleeve with a spherical-like portion protruding out of the inner surface of said sleeve for contact with the outer surface of said core sample.

4. The apparatus of claim 3 wherein each of said electrodes comprises:
   a) a cylindrical main body member,
   b) an end member having a spherical-like portion protruding out the inner surface of said sleeve for making contact with the outer surface of said core sample.

5. The apparatus of claim 4 wherein said end member is recessed adjacent said main body member.

6. The apparatus of claim 4 wherein said end member is semi-spherical with diameter greater than that of said main body member.

7. The apparatus of claim 6 wherein the flat portion of said semi-spherical end member is adjacent to said main body member and normal to the cylindrical axis of said main body member.

8. Apparatus for determining resistivity of a core sample of a fluid saturated porous rock under confining pressure, comprising:
   a) a sleeve containing a core sample of a porous rock saturated with a first fluid,
   b) a fluid inlet positioned in a first end of said sleeve through which a second fluid is injected under pressure into the first end of said core sample for displacing said first fluid from a second end of said core sample, said second fluid being immiscible with said first fluid and of opposite electrical conductance,
   c) a porous member positioned adjacent a second end of said sleeve through which said first fluid is discharged from the second end of said core sample through said porous member,
   d) a fluid inlet positioned in a second end of said sleeve through which said first fluid is discharged from said sleeve after having been displaced from the second end of said core sample through said porous member,
   e) a plurality of electrode arrays extend through said sleeve at spaced-apart positions along the length of said sleeve and make contact with the outer surface of said core sample at said spaced-apart positions, each of said arrays being in a plane normal to said axis and having electrodes equally spaced at an even number of positions about the outer surface of said core sample,
   f) means for passing a current through said core sample,
   g) means for applying a confining pressure through said sleeve to said core sample,
   h) means connected to said electrodes for measuring the voltage across each pair of electrodes that are spaced 180 apart about said core sample in each of said arrays in response to the flow of said current through said fluid saturated core sample at said confining pressure, and i) means for determining resistivities of said core sample from said measured voltages in the plurality of radial directions normal to the core sample for which said voltages were measured.

9. The apparatus of claim 8 further including means for comparing said determined resistivities to identify the radial direction of any electrical anisotropy within said core sample in the plane of each of said electrode arrays and along the length of said core sample between said electrode arrays.

10. The apparatus of claim 8 wherein said electrodes pass through said sleeve and extend outward from the inner surface of said sleeve with a rounded end for making contact with the outer surface of said core sample.

11. The apparatus of claim 8 wherein each of said electrodes comprises:
   a) a cylindrical main body member, and
   b) a spherical-like end member for making contact with the outer surface of said core sample.

12. The apparatus of claim 11 wherein each of said electrodes is molded into said sleeve such that a portion of said spherical-like end member protrudes through the inner surface of said sleeve.

13. The apparatus of claim 12 wherein said spherical-like end member is recessed adjacent to said main body member.

14. The apparatus of claim 13 wherein said spherical-like end member is recessed normally to the outer surface of said cylindrical main body member.

15. The apparatus of claim 12 wherein said end member is semispherical.

* * * * *